(12) United States Patent
Dobbs et al.

(10) Patent No.: US 6,300,326 B1
(45) Date of Patent: Oct. 9, 2001

(54) COMPOSITION AND METHOD FOR CONTROL AND TREATMENT OF CUTANEOUS INFLAMMATION

(76) Inventors: Michael R. Dobbs, 1920 Appomattox Rd., Lexington, KY (US) 40504; T. Reid McArthur, 1903 E. First St., Vidalia, GA (US) 30474

( * ) Notice: Subject to any disclaimer, the term of this patent is extended or adjusted under 35 U.S.C. 154(b) by 0 days.

(21) Appl. No.: 09/631,165

(22) Filed: Aug. 3, 2000

Related U.S. Application Data

(63) Continuation of application No. 08/876,893, filed on Jun. 16, 1997, now abandoned, which is a continuation of application No. 08/333,831, filed on Nov. 2, 1994, now abandoned.

(51) Int. Cl.[7] ............................. A61K 31/56; A61K 7/00; A61K 35/78
(52) U.S. Cl. ............................. 514/171; 424/401; 424/725
(58) Field of Search ............................. 514/171; 424/725, 424/401

(56) References Cited

U.S. PATENT DOCUMENTS

| | | |
|---|---|---|
| 2,951,012 | 8/1960 | Gisvold . |
| 3,886,268 | 5/1975 | Halpern . |
| 4,112,067 | 9/1978 | Tomalia et al. . |
| 4,970,220 * | 11/1990 | Chaussee ........................... 514/358 |
| 5,013,545 | 5/1991 | Blackman et al. . |

OTHER PUBLICATIONS

Martindale, The Extra Pharmacopoeia, 28th ed., p. 286, 1982.*

* cited by examiner

*Primary Examiner*—Raymond Henley, III
(74) *Attorney, Agent, or Firm*—King and Schickli PLLC

(57) ABSTRACT

A composition for treating cutaneous inflammation by topical application comprises a range of percentages of anti-infective solvent, water, an emollient agent, and anti-inflammatory/anti-pruritic agents. The composition is sufficiently viscous to be applied as a spray. There is also disclosed a method of treating the dermal areas of mammals using the composition as a topical medication.

31 Claims, No Drawings

COMPOSITION AND METHOD FOR CONTROL AND TREATMENT OF CUTANEOUS INFLAMMATION

This application is a continuation of U.S. patent application Ser. No. 08/876,893, filed on Jun. 16, 1997, which is now abandoned, which is a continuation of 08/333,831 filed Nov. 2, 1994, now abandoned.

FIELD OF THE INVENTION

The present invention relates generally to compositions for treating cutaneous inflammation by topical application of a corticosteroid containing formulation and, more particularly, to a sprayable composition amenable to treat cutaneous inflammation syndromes such as chronic, non-responsive allergic dermatitis, and a method to treat the dermal areas of mammals with such composition. The composition has the surprising and unexpected benefit of incorporating lower concentrations of active ingredient, allowing longer term use as well as use over larger skin surface areas of afflicted patients with reduced risks to the patients.

BACKGROUND OF THE INVENTION

Many individuals are affected by eczema or inflammation of the skin. A topic dermatitis is the most severe and chronic form of eczema, although there are several other skin conditions that are eczemas including seborrheic dermatitis, irritant contact dermatitis, and allergic contact dermatitis. Skin inflammations may be triggered by any number of factors. For example, irritant contact (such as by solvents, chemicals, detergents, etc.) may trigger eczema. Eczema may also be triggered by allergens, for example by dermal exposure to plant species such as poison ivy, poison oak and poison sumac. Individuals with severe eczema such as a topic dermatitis are often prone to secondary skin infections such as by Staphylococcus bacteria or Herpes virus.

It is known in the art to treat inflammatory and pruritic manifestations of dermatitis syndromes topically with corticosteroids. The mechanism of anti-inflammatory actions of topical corticosteroids has not been completely elucidated. However, it is thought that corticosteroids act by inducing phospholipase $A_2$ inhibitory proteins called lipocortins. Lipocortins may control synthesis of potent mediators of inflammation such as prostaglandins and leukotrienes.

Heretofore, corticosteroid treatments for dermatitis have been topical applications in the form of creams gels, or lotions. These medicamentous vehicles tend to leave a greasy layer on the treated area which can be unpleasant to the recipient. Additionally, the task of preparing the appropriate suspension of active ingredients in a cream, lotion, or gel form can be laborious. Thus, the prior compositions of active medicaments, dispersed in their related delivery media, do not provide an ideal solution for treating dermal inflammation and irritation.

More importantly, corticosteroid treatments for dermatitis have traditionally incorporated higher concentrations of steroid, typically 0.1 percent by weight or higher, to provide beneficial effects. For example, U.S. Pat. No. 4,343,798 teaches use of corticosteroids in combination with $C_5$–$C_{12}$ fatty acids for topical treatment of inflammatory skin conditions. Typical concentrations of corticosteroid taught in the '798 patent include 0.5 percent by weight beclomethasone dipropionate, 0.1 percent by weight hydrocortisone butyrate, 1 percent by weight hydrocortisone with urea, and 0.1 percent by weight triamcinolone acetonide. Similarly, U.S. Pat. No. 4,107,161 teaches use of a triamcinolone isomer at concentrations ranging from 0.1 percent to 0.5 percent by weight.

There are significant disadvantages to prior compositions which utilize corticosteroids in higher concentrations. Systemic absorption of topical corticosteroids may produce a reversible hypothalamic-pituitary-adrenal (HPA) axis suppression with the potential for glucocorticosteroid insufficiency after withdrawal of treatment. Manifestations of Cushing's syndrome, hyperglycemia, and glucosuria may also occur in some patients by systemic absorption of topical corticosteroids during treatment. Pediatric patients, patients receiving treatment with superpotent corticosteroids, patients applying topical steroids over a large skin surface area, and patients applying corticosteroids to areas under occlusion are at particular risk. Due to potentially harmful side effects, current formulations employing corticosteroids for topical treatment of skin inflammation are often limited in terms of the size of the skin area which may be treated and the length of time over which treatment may occur.

Often, however, eczemas (such as allergic contact dermatitis) which are of uncertain origin and chronic in nature manifest in patients, necessitating longer-term treatments and treatments over large skin areas. There is thus need in the art for a corticosteroid treatment for chronic dermatitis which incorporates lower concentrations of corticosteroid and is therefore suitable for longer periods of treatment. There is also need for such a corticosteroid treatment which may be conveniently applied over large skin surface areas without the disadvantages associated with cream or lotion carriers. One such means for avoiding cream or lotion formulations is a dip treatment. However, dipping is unsuitable for larger patients such as humans or large animals due to difficulties in application and the large quantities of medicament required. In response to the need in the art, the applicant has developed a new and improved spray formulation that successfully treats skin conditions such as chronic, non-responsive allergic dermatitis which incorporates reduced concentrations of corticosteroid.

SUMMARY OF THE INVENTION

It is therefore a primary object of the present invention to provide a composition that is effective in treating the inflammation and irritation associated with skin disorders such as dermatitis with pruritic activity.

A further object of the present invention is to provide a composition that is effective in treating inflammation and irritation associated with skin disorders such as dermatitis which incorporates a lower concentration of active ingredient, allowing longer-term treatment with reduced risk to the patient.

Another object of the present invention is to provide a composition that is of an appropriate liquid character to facilitate application in spray form.

Yet another object of the present invention is to provide a composition that is sprayable for topical application and in which the liquid carrier evaporates and leaves the active medicaments in the treated area as a dry film.

Still another object of the present invention is to provide a method of treating dermal areas of mammals that is both pleasant and easy in application and effective in result.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an inventive composition is disclosed having ingredients which, in combination, result in an effective formulation for topically treating the inflammation and irritation associated with such skin conditions as allergic contact dermatitis. The composition preferably contains a range of from about 5.0 percent to about 80.0 percent by volume anti-infective solvent, and from about 10.0 percent to about 90.0 percent by volume water. Denatured lower alcohols such as isopropyl alcohol and ethyl alcohol are desirably used as the solvents. These components when mixed together provide a medium for active medicaments resulting in a sprayable liquid that is used for topical application.

In the particular preferred formulation, the composition includes from about 50 percent to about 80 percent by volume water. Furthermore, the anti-infective solvent ranges from about 5 percent to about 30 percent by volume.

The inventive composition is also contemplated to include from about 5.0 percent to about 40.0 percent by volume emollient agent. It has been determined that the most desired volumetric composition range for this component is from about 10.0 percent to about 30.0 percent. The presently preferred embodiment of the composition utilizes propylene glycol as the emollient agent. It should be appreciated, however, that the compositions envisioned in the present invention may contain, e.g. glycerol, acetylated lanolin alcohol, cetyl alcohol, or any suitable emollient agent known in the art.

The composition may further include from about 2.0 percent to about 7.5 percent by volume astringent agent. Witch hazel is a particularly preferred astringent. However, any suitable astringent known in the art may be incorporated into the compositions of the present invention.

The composition of the present invention may also include from about 0.01 percent to about 0.5 percent by weight of a suitable anti-pruritic agent to address the problem of itching associated with certain dermatoses. A particularly preferred embodiment of the present invention contains menthol. However, it should be appreciated that, e.g., camphor, phenol, or any suitable anti-pruritic known in the art may be used.

The composition preferably also includes from about 0.005 percent to about 0.10 percent by volume of anti-inflammatory agent. Various corticoid compounds are contemplated as being utilized as an antiinflammatory agent in the novel formulation. A preferred example of a topical anti-inflammatory corticoid is triamcinolone acetonide and is included to comprise from about 0.010 percent to about 0.05 percent by volume of the composition.

The preferred composition is used in a method for treating dermal areas of mammals with a topical medication having anti-inflammatory and anti-pruritic activity. The makeup of the composition allows the active medicaments to be sprayed on the specific body area where treatment is desired. The large amount of anti-infective solvent facilitates evaporation of the liquid carrier so as to leave the active medicaments as a film in a dry environment at the treated area.

Still other objects of the present invention will become apparent to those skilled in this art from the following description wherein there is shown and described a preferred embodiment of this invention, simply by way of illustration of one of the modes best suited to carry out the invention. As will be realized, the invention is capable of other different embodiments and its several details are capable of modification in various, obvious aspects, all without departing from the invention. Accordingly, the description will be regarded as illustrative in nature and not as restrictive.

DETAILED DESCRIPTION OF THE INVENTION

A composition in accordance with the teachings of the present invention is provided for topical application in treating the inflammation and irritation of certain dermatoses. The composition is particularly effective in treating cutaneous inflammation resulting from chronic, non-responsive allergic dermatitis.

The composition is preferably formulated as a liquid of a character that is adapted to be sufficiently thin to allow spray application but not so thin as to flow away from the treated area upon such application. The liquid medium is preferably formulated as a mixture with from about 5.0 percent to about 80.0 percent by volume anti-infective solvent, such as isopropyl alcohol or ethyl alcohol, and from about 10.0 percent to about 90.0 percent by volume water. In a presently preferred embodiment, these components range from about 5.0 percent to about 30.0 percent by volume anti-infective solvent and from about 50.0 percent to about 80.0 percent by volume water. It is most desirable to use sterile water in the formulation, although a lesser grade of purified water is sufficient for the functional purposes of the invention. These liquid ingredients may be obtained from a variety of well-known supply sources such as chemical and medical supply enterprises.

This mixture of liquids presents an ideal balance for facilitating spray application and permitting evaporation at a rate for allowance of the active medicaments to penetrate the treated skin area, yet minimizing the run-off of applied composition from the treated area. Furthermore, the antiseptic quality of the solvent is not substantially inhibited within this concentration range.

The inventive composition also preferably incorporates an emollient agent to soften and soothe the treated area. The preferred concentration range for the emollient agent is from about 5.0 percent to about 40.0 percent by volume. The particular preferred composition is formulated with propylene glycol as the emollient agent in a range of from about 10.0 percent to about 30.0 percent by volume. However, it should be appreciated that other emollient agents, such as glycerol, are also suitable for incorporation into the compositions of the present invention.

Inflammation is commonly associated with many dermatoses. It is thus desirable to include in the inventive composition a pharmaceutically effective amount of an anti-inflammatory agent. It has been determined that the amount be within a range from about 0.005 percent to about 0.10 percent by volume. Corticoid compounds have proven to be effective anti-inflammatory agents and are thus most desirable for inclusion in the inventive composition. Corticoid compounds are any of the various adrenal cortex steroids that may be isolated in naturally occurring matter or synthetically produced. Examples of corticoid compounds that are alternatively includable in the composition are hydrocortisone, triamcinolone and dexamethasone. Of these corticoid compounds, triamcinolone has been found to be the most favorable for use in a presently preferred embodiment of the invention in an amount of substantially 0.015 percent by volume. Triamcinolone may be supplied in the form of triamcinolone acetonide.

As stated above, the inventive composition is particularly useful in a method of treating dermal areas of mammals with a topical application having anti-inflammatory and anti-pruritic activity. It is particularly easy to use in that it is amenable to spray application. The liquid formulation is also sufficiently viscous so as to remain in the area of application. The anti-infective solvent is of adequate concentration to be effective as an antiseptic while evaporating to leave the treated area in a dry environment. The inventive composition thus provides a desirable alternative to previous methods of treatment involving ointments, lotions or creams for topical use. The present invention is further desirable in that it incorporates lower concentrations of active ingredient, reducing risk to the patient during longer term treatment.

EXAMPLES

The following examples are intended to be illustrative of the invention, and are not to be considered restrictive of the scope of the invention as otherwise described herein.

Example 1

A typical production batch preparation of a presently preferred embodiment of the invention is described below.

A. Approximately 171 grams of Triamcinolone acetonide.
B. Approximately 113.6 kg denatured alcohol.
C. Approximately 227.1 kg propylene glycol
D. Approximately 5.68 kg dimethyldimethyl hydantoin
E. Approximately 788.95 kg purified water

Example 2

An in vivo model of cutaneous inflammation was developed for the dog, and used to evaluate the anti-inflammatory effect of a presently preferred embodiment of the current invention. Healthy dogs (n=3) were treated on one side of the lateral thorax with the present invention, and on the contralateral side with vehicle solution. After 7 days of treatment, serial dilutions of inflammatory stimuli (histamine, compound 48/80, anti-canine IgE, substance P, and morphine sulfate) were injected intradermally on both sides. Resulting immediate reactions were subjectively scored, their diameters were measured in millimeters, and microcirculatory blood flow at each site was measured using laser Doppler velocimetry. The magnitude of the differences between treated and placebo sides varied with the type of measurement and the stimulus used. With compound 48/80, anti-IgE, substance P, and morphine sulfate-injected sites, for at least one concentration, the reaction scores and sizes were notably less on the treated sides. Punch skin biopsy specimens were obtained from selected sites 24 hours after injection. A pathologist examined stained tissue sections and scored each section as to degree of dermal cellular infiltrate. Dermal infiltrate scores were generally lower at the treated sites; the composite score from all treated sites was 30% lower than that from the placebo-treated sites.

Example 3

A placebo-controlled, double-blind trial was conducted to determine the efficacy of a preferred embodiment of the current invention in dogs, for reducing clinical signs of pruritic skin diseases with a proven or suspected allergic basis. Dogs underwent diagnostic evaluation and/or treatment to eliminate parasitic or infectious causes of pruritus prior to entry. Ninety-six dogs at five centers were entered into the 4-week trial and randomly assigned to treatment with the present invention or vehicle. Treatment was performed by spraying affected areas of the body twice daily for 1 week, then once daily for 1 week, then every other day for 2 weeks. Hemograms, serum chemistry analyses, and clinical sign scores for pruritus, erythema, and lesions (performed by both the owner and the veterinarian) were obtained before and after treatment. Eighty-nine animals (44 drug, 45 vehicle) completed the study.

Treatment success (reduction in overall clinical score of 2 grades on a 6-point scale) was achieved in 65.9% of dogs treated with the present invention and 26.7% of vehicle-treated dogs. Owners rated the present invention as "very effective" in 59.1% of cases, vs. 27.7% for vehicle. Alterations in serum chemistry and hemograms occurred sporadically in both treatment groups. In this trial, the present invention proved to be an unexpectedly efficacious short-term treatment for allergic pruritus in many dogs, with a low prevalence of glucocorticoid-related adverse effects.

In summary, numerous benefits result from topical application of the inventive composition in treating dermal areas of mammals. The liquid character of the composition allows it to be easily applied to the treated area in the form of a spray. It is nevertheless sufficiently viscous to remain in the area of application to optimally achieve its purpose. The solvent evaporates to leave the active medicaments in a dry environment. This is in contrast to the oily or greasy feel resulting from ointments, lotions or creams. The active ingredients are thus applied to the affected area directly and quickly to promote relief from irritation and inflammation.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

What is claimed is:

1. A composition for topical use in treating cutaneous inflammation, comprising:
   from about 5.0 percent to about 80.0 percent by volume anti-infective solvent;
   from about 10.0 percent to about 90.0 percent by volume water;
   from about 5.0 percent to about 40.0 percent by volume emollient agent;
   from about 2.0 percent to about 7.5 percent astringent agent;
   from about 0.1 percent to about 0.5 percent anti-pruritic agent;
   from about 0.1 percent to about 1 percent preservative; and
   from about 0.005 percent to about 0.10 percent by volume anti-inflammatory agent.

2. The composition as in claim 1, which comprises from about 5 percent to about 30 percent by volume anti-infective solvent.

3. The composition as in claim 1, which comprises from about 50 percent to about 80 percent by volume water.

4. The composition as in claim 1, which comprises from about 10 percent to about 30 percent by volume emollient agent.

5. The composition as in claim 1, which comprises from about 4.8 percent to about 5.3 percent by volume astringent agent.

6. The composition as in claim 1, which comprises from about 0.08 percent to about 0.12 percent by volume anti-pruritic agent.

7. The composition as in claim 1, which comprises from about 0.25 percent to about 0.75 percent by volume preservative.

8. The composition as in claim 1, which comprises substantially about 0.010 percent to about 0.05 percent by volume anti-inflammatory agent.

9. The composition as in claim 1, wherein said anti-infective solvent is selected from the group consisting of denatured isopropyl alcohol and ethyl alcohol.

10. The composition as in claim 1, wherein said emollient agent is selected from the group consisting of propylene glycol and glycerol.

11. The composition as in claim 1, wherein said astringent agent is witch hazel.

12. The composition as in claim 1, wherein said anti-pruritic agent is selected from the group consisting of menthol, camphor, and phenol.

13. The composition as in claim 1, wherein said preservative is dimethyldimethylhydantoin.

14. The composition as in claim 1, wherein said anti-inflammatory agent is selected from the group of corticosteroids consisting of triamcinolone acetonide, triamcinolone, hydrocortisone, cortisone, beclamethasone, cortodoxone, flucetonide, fluorocortisone, difluorosone diacetate, medrysone, amcinafel, amcinafide, betamethasone, esters of betamethasone, chloroprednisone, clocortelone, descinolone, desonide, defluprednate, flucloronide, flumethasone, flunisolide, fluocinonide, flucortolone, fluperolone, fluprednisolone, meprednisone, methyl prednisone, paramethasone, prednisolone, prednidone, hydrocortamate, dichlorisone, methylprednisone, fluorocortisone, dexamethasone, fluroandrenolone acetonide, fluocinolone acetonide, fluorametholone, and dichlorisone.

15. The composition as in claim 1, wherein said anti-inflammatory agent is triamcinolone acetonide.

16. A method of treating cutaneous inflammation in mammals with a composition having anti-inflammatory/anti-pruritic activity, said method comprising topical application of a composition comprising:
   from about 5.0 percent to about 80.0 percent by volume anti-infective solvent;
   from about 10.0 percent to about 90.0 percent by volume water;
   from about 5.0 percent to about 40.0 percent by volume emollient agent;
   from about 2.0 percent to about 7.5 percent astringent agent;
   from about 0.01 percent to about 0.5 percent anti-pruritic agent;
   from about 0.1 percent to about 1 percent preservative; and
   from about 0.005 percent to about 0.10 percent by volume anti-inflammatory agent.

17. The method as in claim 16, wherein said composition is of an appropriate liquid character so as to be applied as a spray.

18. The method as in claim 16, wherein said composition includes from about 5 percent to about 30 percent by volume anti-infective solvent.

19. The method as in claim 16, wherein said composition includes from about 50 percent to about 80 percent by volume water.

20. The method as in claim 16, wherein said composition includes from about 10 percent to about 30 percent by volume emollient agent.

21. The method as in claim 16, wherein said composition includes from about 4.8 percent to about 5.3 percent by volume astringent agent.

22. The method as in claim 16, wherein said composition includes from about 0.08 percent to about 0.12 percent by volume anti-pruritic agent.

23. The method as in claim 16, wherein said composition includes from about 0.25 percent to about 0.75 percent by volume preservative.

24. The method as in claim 16, wherein said composition includes from about 0.010 percent to about 0.05 percent by volume anti-inflammatory agent.

25. The method as in claim 16, wherein said anti-infective solvent in said composition is selected from the group consisting of denatured isopropyl alcohol and ethyl alcohol.

26. The method as in claim 16, wherein said emollient agent in said composition is selected from the group consisting of propylene glycol and glycerol.

27. The method as in claim 16, wherein said astringent agent in said composition is witch hazel.

28. The method as in claim 16, wherein said anti-pruritic agent in said composition is selected from the group consisting of menthol, camphor, and phenol.

29. The method as in claim 16, wherein said preservative in said composition is dimethyldimethylhydantoin.

30. The method as in claim 16, wherein said anti-inflammatory agent in said composition is selected from the group of corticosteroids consisting of triamcinolone acetonide, triamcinolone, hydrocortisone, cortisone, beclamethasone, cortodoxone, flucetonide, fluorocortisone, difluorosone diacetate, medrysone, amcinafel, amcinafide, betamethasone, esters of betamethasone, chloroprednisone, clocortelone, descinolone, desonide, defluprednate, flucloronide, flumethasone, flunisolide, fluocinonide, flucortolone, fluperolone, fluprednisolone, meprednisone, methyl prednisone, paramethasone, prednisolone, prednidone, hydrocortamate, dichlorisone, methylprednisone, fluorocortisone, dexamethasone, fluroandrenolone acetonide, fluocinolone acetonide, fluorametholone, and dichlorisone.

31. The method as in claim 16, wherein said anti-inflammatory agent in said composition is triamcinolone acetonide.

* * * * *

UNITED STATES PATENT AND TRADEMARK OFFICE
CERTIFICATE OF CORRECTION

PATENT NO.    : 6,300,326 B1  
DATED         : October 9, 2001  
INVENTOR(S)   : Michael R. Dobbs and T. Reid McArthur Page 1 of 1

It is certified that error appears in the above-identified patent and that said Letters Patent is hereby corrected as shown below:

<u>Column 6,</u>
Line 57, replace "0.1" with -- 0.01 --

Signed and Sealed this

Seventh Day of May, 2002

Attest:

Attesting Officer

JAMES E. ROGAN
Director of the United States Patent and Trademark Office